(12) United States Patent
Wood et al.

(10) Patent No.: US 8,887,730 B2
(45) Date of Patent: Nov. 18, 2014

(54) DUAL-LUMEN TRACHEAL TUBE WITH ASSEMBLY PORTION

(75) Inventors: Lockett E. Wood, Lyons, CO (US);
Sarah Hayman, Boulder, CO (US)

(73) Assignee: Covidien LP, Cupertino, CA (US)

( * ) Notice: Subject to any disclaimer, the term of this patent is extended or adjusted under 35 U.S.C. 154(b) by 658 days.

(21) Appl. No.: 13/116,901

(22) Filed: May 26, 2011

(65) Prior Publication Data

US 2012/0298111 A1  Nov. 29, 2012

(51) Int. Cl.
*A61M 11/00* (2006.01)
*A61M 16/04* (2006.01)

(52) U.S. Cl.
CPC ....... *A61M 16/0434* (2013.01); *A61M 16/0486* (2014.02); *A61M 16/0459* (2014.02); *A61M 16/0404* (2014.02)
USPC ............. 128/207.14; 128/207.15; 128/207.16

(58) Field of Classification Search
CPC ............ A61M 16/04; A61M 16/0434; A61M 16/0463
USPC ........................... 128/207.14–207.16, 200.26
See application file for complete search history.

(56) References Cited

U.S. PATENT DOCUMENTS

| | | | |
|---|---|---|---|
| 3,884,242 A * | 5/1975 | Bazell et al. | 128/207.15 |
| 3,964,488 A | 6/1976 | Ring et al. | |
| 4,305,392 A | 12/1981 | Chester | |
| 4,685,457 A | 8/1987 | Donenfeld | |
| 4,846,153 A | 7/1989 | Berci | |
| 4,949,716 A | 8/1990 | Chenoweth | |
| 4,982,729 A | 1/1991 | Wu | |
| 4,995,388 A | 2/1991 | Brain | |
| 5,016,614 A | 5/1991 | MacAllister | |
| 5,038,766 A | 8/1991 | Parker | |
| 5,174,283 A | 12/1992 | Parker | |
| 5,203,320 A | 4/1993 | Augustine | |
| 5,245,992 A * | 9/1993 | Nye | 128/200.26 |
| 5,259,377 A | 11/1993 | Schroeder | |
| 5,285,778 A | 2/1994 | Mackin | |
| 5,315,992 A * | 5/1994 | Dalton | 128/207.15 |
| 5,329,940 A | 7/1994 | Adair | |

(Continued)

FOREIGN PATENT DOCUMENTS

WO  WO9422518  10/1994

OTHER PUBLICATIONS

Campos, Javier H. MD et al., Comparison of a Modified Double-Lumen Endotracheal Tube with a Single-Lumen Tube with Enclosed Bronchial Blocker, International Anesthesia Research Society, 1996, pp. 1268-1272, Issue 83.
Mallinckrodt, Tyco Healthcare, Endobronchial Tubes, Jul. 2001.

(Continued)

*Primary Examiner* — Steven Douglas
(74) *Attorney, Agent, or Firm* — Fletcher Yoder PC

(57) ABSTRACT

The present disclosure describes systems and methods having a dual-lumen tube with an assembly end. The assembly end may be molded and coupled to an extruded portion of the tube to form a complete dual-lumen tube. The assembly end may form the distal portion of the dual-lumen tube, which may simplify the manufacturing process by eliminating cutting and shaping steps involved in forming the distal ends of the ventilation lumens. The assembly end may be molded or otherwise formed so that the distal portion is not cut to length. In addition, the assembly end may include addition functionality, such as a camera apparatus or one or more sensors.

19 Claims, 5 Drawing Sheets

(56) References Cited

U.S. PATENT DOCUMENTS

| | | | |
|---|---|---|---|
| 5,333,608 A | 8/1994 | Cummins | |
| 5,339,805 A | 8/1994 | Parker | |
| 5,400,771 A | 3/1995 | Pirak et al. | |
| 5,429,127 A | 7/1995 | Kolobow | |
| 5,582,167 A | 12/1996 | Joseph | |
| 5,588,424 A * | 12/1996 | Insler et al. | 128/207.15 |
| 5,607,386 A | 3/1997 | Flam | |
| 5,636,625 A | 6/1997 | Miyagi et al. | |
| 5,694,929 A | 12/1997 | Christopher | |
| 5,785,051 A | 7/1998 | Lipscher et al. | |
| 5,819,723 A | 10/1998 | Joseph | |
| 5,921,917 A | 7/1999 | Barthel et al. | |
| 5,954,636 A | 9/1999 | Schwartz et al. | |
| 5,964,217 A | 10/1999 | Christopher | |
| 6,142,144 A | 11/2000 | Pacey | |
| 6,189,533 B1 | 2/2001 | Simon et al. | |
| 6,196,225 B1 | 3/2001 | Allgeyer | |
| 6,318,367 B1 | 11/2001 | Mongeon | |
| 6,443,156 B1 * | 9/2002 | Niklason et al. | 128/207.14 |
| 6,520,183 B2 * | 2/2003 | Amar | 128/207.14 |
| 6,543,446 B1 | 4/2003 | Christopher | |
| 6,568,388 B2 | 5/2003 | Christopher | |
| 6,631,713 B1 | 10/2003 | Christopher | |
| 6,672,305 B2 | 1/2004 | Parker | |
| 6,849,042 B2 | 2/2005 | Christopher | |
| 6,860,264 B2 | 3/2005 | Christopher | |
| 6,929,600 B2 | 8/2005 | Hill | |
| 6,961,600 B2 | 11/2005 | Kohl et al. | |
| 7,013,899 B2 * | 3/2006 | Alfery et al. | 128/207.18 |
| 7,052,456 B2 | 5/2006 | Simon | |
| 7,921,847 B2 * | 4/2011 | Totz | 128/207.15 |
| 7,938,119 B2 * | 5/2011 | Chen et al. | 128/207.15 |
| 8,573,218 B2 * | 11/2013 | Rutter | 128/207.14 |
| 2004/0221853 A1 | 11/2004 | Miller | |
| 2006/0025650 A1 | 2/2006 | Gavriely | |
| 2006/0081255 A1 | 4/2006 | Miller et al. | |
| 2006/0253197 A1 | 11/2006 | NaPier | |
| 2008/0142003 A1 | 6/2008 | Depel | |
| 2010/0030057 A1 | 2/2010 | Gavriely et al. | |
| 2012/0024292 A1 * | 2/2012 | Sandmore et al. | 128/207.14 |
| 2012/0172664 A1 | 7/2012 | Hayman et al. | |
| 2012/0179009 A1 | 7/2012 | Gavriely | |
| 2012/0298111 A1 | 11/2012 | Wood et al. | |

OTHER PUBLICATIONS

Ayoub, CM et al., Advancing the Tracheal Tube Over a Flexible Fiberoptic Bronchoscope by a Sleeve Mounted on the Insertion Cord, Department of Anesthesiology, PubMed, Jan. 2003. pp. 1-4.

* cited by examiner

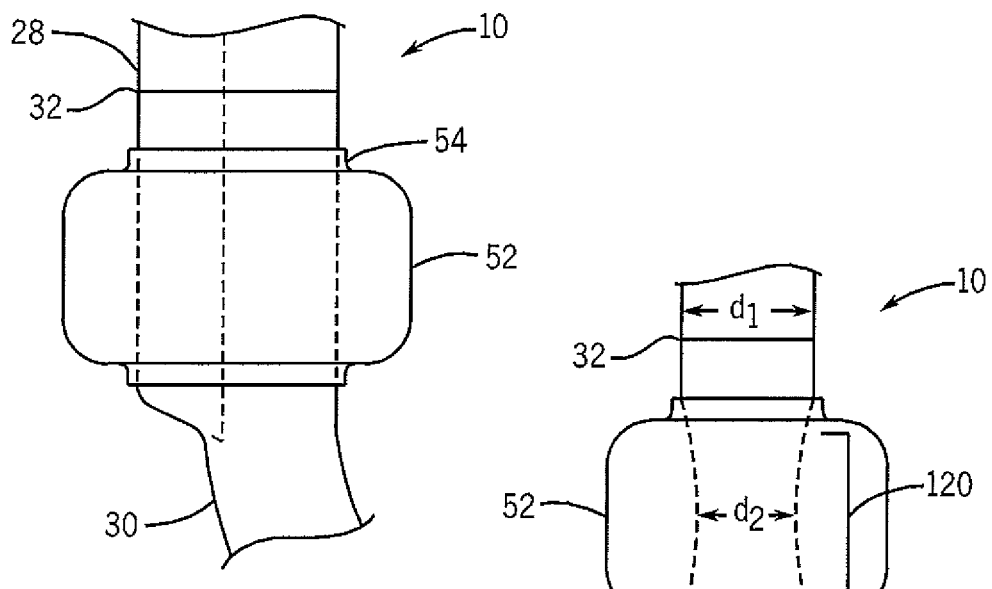
FIG. 4
FIG. 5
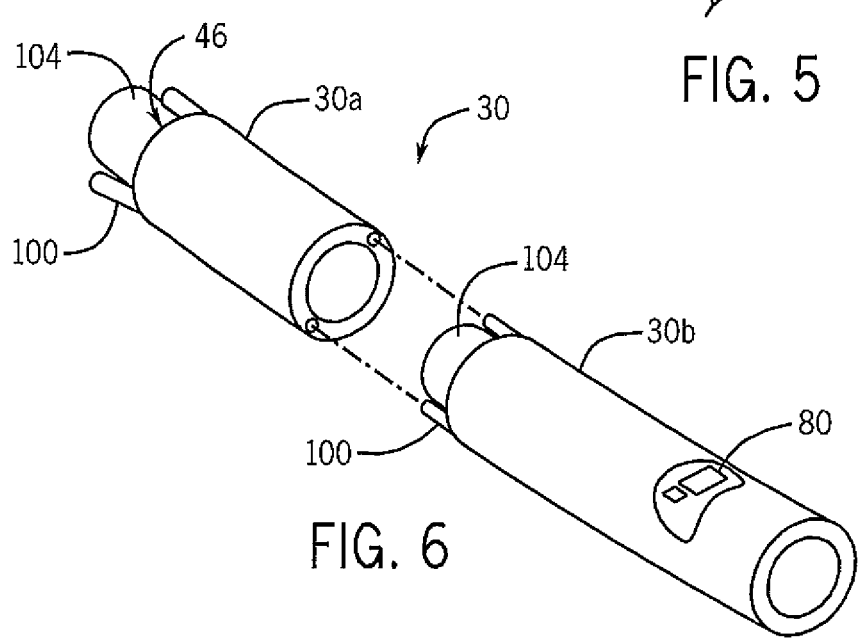
FIG. 6

DUAL-LUMEN TRACHEAL TUBE WITH ASSEMBLY PORTION

BACKGROUND

The present disclosure relates generally to medical devices and, more particularly, to dual-lumen tracheal tubes that may accommodate an integral visualization device, such as a camera.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tracheal tube (e.g endotracheal, nasotracheal, or transtracheal device) may be used to control the flow of gases into the trachea of a patient. Often, a seal between the outside of the tube and the interior wall of the tracheal lumen is required, allowing for generation of positive intrathoracic pressure distal to the seal and prevention of ingress of solid or liquid matter into the lungs from proximal to the seal.

Depending on the clinical condition of the patient, ventilation may involve a tracheal tube capable of ventilating one lung to the exclusion or independently of the other. For example, during thoracic surgery, surgeons may wish to isolate and perform surgery on an affected lung while simultaneously ventilating the healthy lung, in order to optimize the surgical field and/or avoid cross-contamination. Endobronchial tubes that allow independent control of each lung through dual lumens are typically used for this purpose. One lumen is opened to ambient pressure to isolate the desired lung, while respiratory and anesthetic gases are delivered via positive pressure ventilation through the other lumen.

Regardless of the particular form, it has become of increasing interest in the field to provide various more complex and, in some cases, interactive devices on such ventilation tubes. For example, proposals have been made to dispose cameras, lighting systems, sensors, and so forth at various intermediate and distal locations on the tubes to aid in such functions as placement visualization, air and tissue monitoring, placement detection. In most cases, such proposals have included various manufacturing steps involving cutting, shaping, forming or otherwise manipulating the tubes themselves. While such operations may be suitable in many cases, they do result in considerable investment in the tubes. Should any late manufacturing process on the tubes be unsatisfactory, the entire assembly may be discarded. Similarly, such manufacturing approaches may severely limit the design options and complexity of the devices that can be formed, assembled, and deployed in conjunction with the tubes.

BRIEF DESCRIPTION OF THE DRAWINGS

Advantages of the disclosed techniques may become apparent upon reading the following detailed description and upon reference to the drawings in which:

FIG. 4 is an elevational view of an exemplary endobronchial tube having a coupling site for the assembly end located proximal to the tracheal cuff;

FIG. 5 is an elevational view of an exemplary tracheal tube with a reduced diameter region within the assembly end;

FIG. 6 is an exploded view of an exemplary assembly end including a subassembly with a camera.

DETAILED DESCRIPTION OF SPECIFIC EMBODIMENTS

Figure 1:
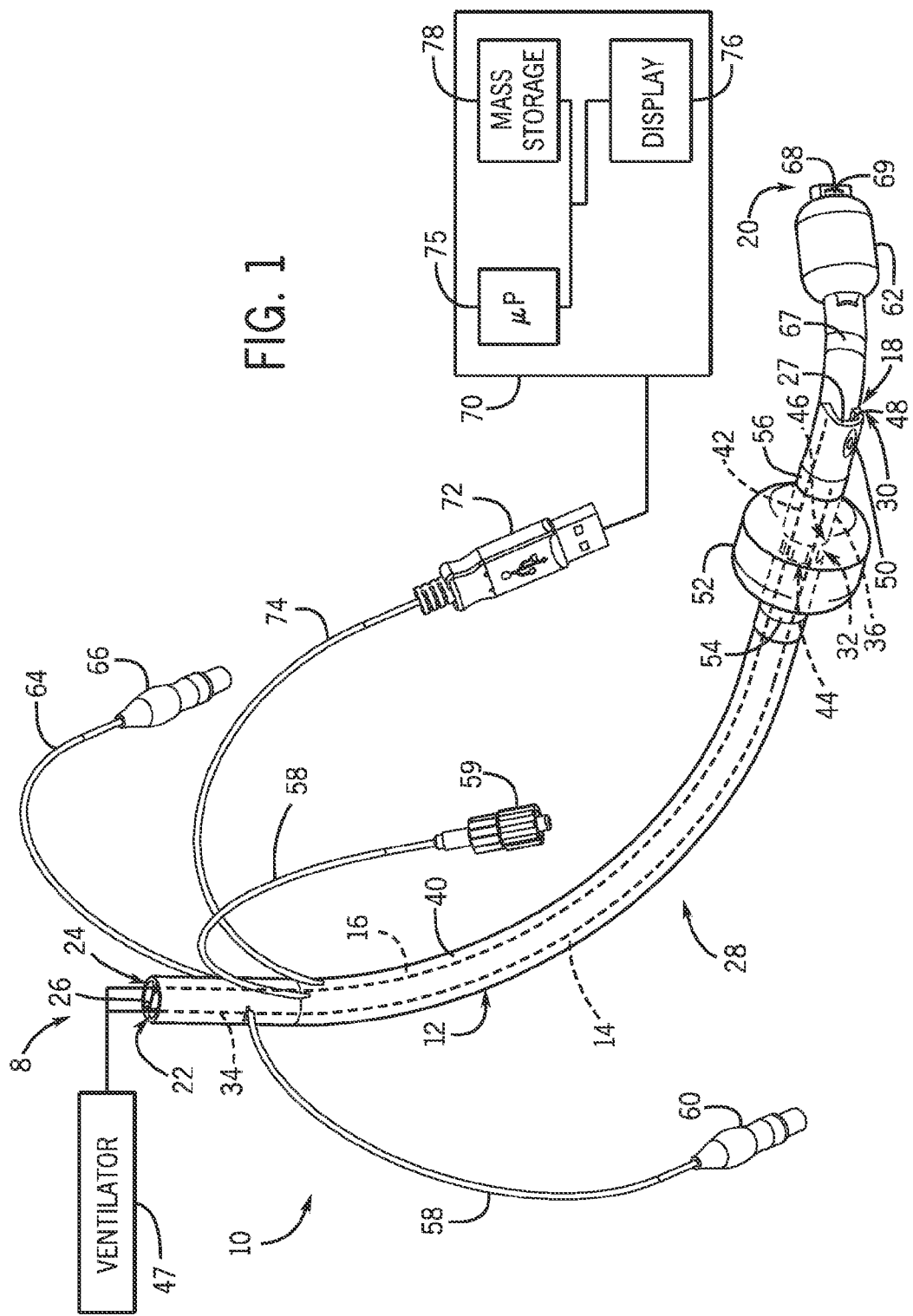
FIG. 1 is a system including an endobronchial tube with an assembly end in accordance with aspects of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, embodiments of tracheal tubes having an assembly end are provided herein. In certain embodiments, the assembly end is coupled to a proximal tube portion to form one or more ventilation lumens of the tracheal tube. In this manner, a simpler portion of the tracheal tube (e.g., one involving fewer manufacturing steps or components) may be formed by a relatively inexpensive process (e.g., extrusion), while a more complicated portion of the tracheal tube (e.g., one involving more manufacturing steps and components) may be contained in the assembly end. Accordingly, the cost of manufacturing the assembly end is limited to only a section of the tracheal tube. For example, one or more ventilation lumens may be formed by coupling an extruded piece and the assembly end. In a particular embodiment, the extruded piece forms a more proximal portion of the tracheal tube and the assembly end forms a more distal portion of the tracheal tube. The present embodiments provide more cost-effective manufacturing solutions and increased flexibility. For example, different types of assembly ends may be selected depending on the desired functionality or geometry of the end product.

In particular, tracheal tubes are typically formed by extrusion, which allows generally uniform sections to be cut from a continuous longer tube. However, after a section is cut from an extrusion, additional cutting and manufacturing steps may be performed. For example, in a particular embodiment, the tracheal tube may be an endobronchial tube. Endobronchial tubes are double-lumen tracheal tubes that facilitate an airtight seal in the trachea and one stem of a patient bronchus to allow independent ventilation of one lung. Generally, an endobronchial tube includes two tubes of unequal length that are attached to one another. One tube terminates within the tracheal airway space, i.e., the shorter tube has a distal end at a location similar to a typical endotracheal tube. The other, longer, tube is configured to extend past the shorter tube and into a left or right bronchial stem. Both tubes define a passageway for transferring gases to and from a patient. To form the endobronchial tube in a typical fabrication, the tracheal ventilation lumen and the bronchial ventilation lumen are extruded together and then the tracheal lumen is shortened by cutting back to a different length. Then, these ends of different lengths are further shaped. The cutting and shaping steps may be numerous, adding to the manufacturing complexity for an endobronchial tube.

As provided herein, rather than cutting and shaping the tracheal and ventilation lumen ends from the extruded tube, these ends may be formed by a molding or other manufacturing process. That is, the distal end of the tube may be molded in the appropriate shape rather than cut and heat-shaped. Once formed, this assembly end may be coupled to a proximal extruded piece. Because the assembly end may be molded into its final desired shape, use of an assembly end may eliminate several cutting and shaping steps that may add to the complexity of tube manufacturing. This provides the further benefit of a more uniformly shaped distal end. In certain embodiments, an assembly end (e.g., a molded piece) as provided may be associated with improved manufacturing accuracy, which in turn may increase manufacturing yield relative to a heat-shaped end that is individually cut and formed for each tube. Further, because a molded piece may allow more complex manufacturing processes to be implemented, the assembly end may also include integral sensors and/or visualization devices (e.g., for corroboration of tube placement) that are incorporated into body of the assembly end and that are easily coupled to the extruded portion of the tube.

The assembly end or assembly portion may form any suitable portion of a tracheal tube, such as the distal end, the proximal end, or an interior portion of the tube, depending on the location of any complex shape or functionality of the tube. In particular embodiments, use of an assembly portion may achieve a more streamlined manufacturing process for particular tube geometries or for tubes with associated sensors or visualization devices. In certain embodiments, an assembly portion may be used to achieve tube geometries or to incorporate certain materials that are incompatible with a simple extrusion process. In other embodiments, assembly portions may carry integral sensors or a camera. In contrast to an extruded tube in which any associated electronic components are typically incorporated after the extrusion is complete, an assembly portion may be formed with integral electronic components that are present in a molded component, or included in an assembly. The resulting structure may permit much more complex or sensitive devices to be formed, with consequent investment made, separately from the manipulation of the tube itself, with the two being joined relatively late in the manufacturing processes.

The tracheal tubes as provided herein are disposable rather than reusable, capable of providing differential mechanical ventilation to either or both lungs, and capable of supporting all other functions of standard endotracheal tubes (e.g. sealing, positive pressure generation, suctioning, irrigation, drug instillation, etc). The tracheal tubes can be used in conjunction with all acceptable auxiliary airway devices such as (e.g. heat and humidity conservers, mechanical ventilators, humidifiers, closed suction systems, scavengers, capnometers, oxygen analyzers, mass spectrometers, PEEP/CPAP devices, etc).

Furthermore, although the embodiments of the present disclosure illustrated and described herein are discussed in the context of endotracheal tubes such as endobronchial tubes, it should be noted that presently contemplated embodiments may include an assembly end or assembly portion associated with any of a variety of suitable airway devices. For example, an assembly end as provided herein may be associated with a single-lumen tube, tracheostomy tube, a Broncho-Cath™ tube, a specialty tube, or any other airway device with a main ventilation lumen. Indeed, any device with a ventilation lumen designed for use in an airway of a patient may include an assembly portion (e.g., an assembly end or an assembly distal end). As used herein, the term "tracheal tube" may include an endotracheal tube, a tracheostomy tube, a Broncho-Cath™ tube, a bronchoblocking tube, a specialty tube, or any other airway device. In addition, assembly ends as provided may be incorporated into catheters or other inserted or implantable medical devices.

Turning now to the drawings, FIG. 1 is a perspective view of a system 8 including an exemplary endobronchial tracheal tube 10 configured to be placed in a patient bronchial stem in accordance with aspects of the present disclosure. The tracheal tube 10 includes a central tubular body 12 with a tracheal ventilation lumen 14 and a bronchial ventilation lumen 16. The tracheal lumen terminates at a tracheal lumen distal end 18 while the bronchial lumen terminates in a bronchial lumen distal end 20. Furthermore, the tracheal tube 10 may include a tracheal lumen proximal end 22 and a bronchial lumen proximal end 24. As shown, the tracheal ventilation lumen 14 and a bronchial ventilation lumen 16 may be attached to one another over a portion of the tubular body 12 and may separate at their respective proximal ends 22, 24 and distal ends 18, 20. Over the portion of the tubular body 12 in which the tracheal ventilation lumen 14 and a bronchial ventilation lumen 16 are attached, the tubular body 12 may include a separating wall 26.

The tubular body 12 includes a proximal portion 28 and an assembly end 30 that are coupled to one another at coupling site 32 to form the tracheal tube 10. The proximal portion 28 and the assembly end 30 are both dual-lumen structures that are coupled together to form the tracheal ventilation lumen 14 and the bronchial ventilation lumen 16. The proximal portion 28 includes a more proximal portion 34 of the tracheal ventilation lumen 14, and the assembly end 30 includes a more distal portion 36 of the tracheal ventilation lumen 14. Similarly, the proximal portion 28 includes a more proximal portion 40 of the ventilation lumen 16, and the assembly end 30 includes a more distal portion 42 of the ventilation lumen 16.

The proximal portion 28 may be formed by extrusion. In such an embodiment, the extruded proximal portion 28 forms a dual-lumen structure with side-by-side portions of the tracheal ventilation lumen 14 and the bronchial ventilation lumen 16 that are separated by wall 26. In embodiments in which the proximal portion 28 is extruded, the distal end 44 of the extruded portion 28 is cut such that the more proximal portion 34 of the tracheal ventilation lumen 14 and the more proximal portion 40 of the bronchial ventilation lumen 16 terminate at substantially the same location, i.e., distal end 44. This distal end is then coupled to a proximal end 46 of the assembly end 30.

The assembly end 30 may be formed by any suitable manufacturing process. In a particular embodiment, the assembly end 30 is formed via molding, e.g. injection molding, overmolding, or transfer molding. In other embodiments, the assembly end 30 is formed, machined, or cast. Many processes may be envisioned for assemblies and components that may be affixed to the distal tube end, including relatively complex and/or sensitive devices that are assembled from mechanical and/or electrical subcomponents. In a specific embodiment, the assembly end 30 may also be formed at least in part via an extrusion process. The proximal portion 28 and the assembly end 30 may be formed from different materials. In particular embodiment, the assembly end 30 may be formed from materials that, when molded into shape, provide suitable rigidity and biocompatibility to the tubular body 12. In other embodiments, the assembly end 30 may be formed from the same materials as the proximal portion 28, but with additional additives or components. In this manner, the additional of relatively expensive additives (e.g., to promote rigidity or electrical conductivity) may be limited to only a portion of the tubular body 12. Further, the assembly end may be formed to align with the proximal portion 28, and may include portions of the tracheal ventilation lumen 14 and the bronchial ventilation lumen 16 as well as any additional cuff inflation lumens. Because the tracheal cuff inflation lumen 58 need not extend past the proximal portion 28, the assembly end 30 may be manufactured without a corresponding section of the lumen 58.

The tracheal lumen proximal end 22 and a bronchial lumen proximal end 24 are located on the proximal portion 28 and may be outfitted with separate connectors that may be attached to a ventilation device 47 during operation that may include a suitable controller (e.g., a processor-based control system) so that a clinician may direct airflow to and from both the tracheal ventilation lumen 14 and bronchial ventilation lumen 16. In other embodiments, either tracheal ventilation lumen 14 or the bronchial ventilation lumen 16 may be blocked or otherwise closed such that only one of the two lumens of the tracheal tube 10 is operational.

The assembly end 30 includes the tracheal lumen distal end 18 that terminates in an opening 48. A Murphy eye 50 may be located on the ventilation lumen 14 opposite the opening 48 to prevent airway occlusion when the tracheal tube assembly 10 is improperly placed within the patient's trachea. As illustrated, a tracheal cuff 52 may encircle the tubular body 12 and be inflated to seal against the walls of a body cavity (e.g., a trachea). The tracheal cuff 52 includes a proximal shoulder 54 that is coupled to the proximal portion 28 and a distal shoulder 56 that is coupled to the assembly end 30. In such an embodiment, the coupling site 32 is substantially encircled by the tracheal cuff 52.

The cuff 52 may be inflated via an inflation lumen terminating in an inflation tube 58 connected to an inflation pilot balloon and valve assembly 60. Additionally, it should be noted that the cuff 52 may be any suitable cuff, such as a tapered cuff, a non-tapered cuff, and so forth. The tracheal ventilation lumen 14 may also include a suction lumen (not shown) that extends from a location on the tracheal tube 10 positioned outside the body when in use to a location on the tubular body 12 that terminates in a port located proximally to cuff 52 through which secretions may be aspirated. As noted, the bronchial ventilation lumen 16 is longer than tracheal ventilation lumen 14 and includes a distal portion 20 that extends past the tracheal lumen distal end 18. The bronchial ventilation lumen 16 may include a bronchial inflation cuff 62 that is configured to seal against the walls of a patient's bronchial stem. The cuff 62 may be inflated via an inflation lumen terminating in an inflation tube 64 connected to an inflation pilot balloon and valve assembly 66.

The tubular body 12 and the cuffs 52 and 62 may be formed from materials having desirable mechanical properties (e.g., puncture resistance, pin hole resistance, tensile strength, and so forth) and desirable chemical properties (e.g., biocompatibility). Further, in one embodiment, the walls of the cuffs 52 and 62 may be made of a polyurethane (e.g., Dow Pellethane® 2363-80A) having suitable mechanical and chemical properties. In other embodiments, the walls of the cuffs 52 and 62 may be made of silicone or a suitable polyvinyl chloride (PVC). In certain embodiments, the cuffs 52 and 62 may be generally sized and shaped as a high volume, low pressure cuff (e.g., a barrel-shaped or tapered cuff) that may be designed to be inflated to pressures between about 15 cm $H_2O$ and 30 cm $H_2O$. Further, bronchial cuff 62 may be a different color or include other identifying markings that allow a user to differentiate between the tracheal cuff 52 and the bronchial cuff 62. In addition, to assist in proper placement of the tube 10, x-ray visible markings 67 may be placed at any appropriate location. For example, the markings 67 may outline a bronchial distal opening 68 or a side eye 69.

In certain embodiments, the assembly end 30 may include one or more sensors or visualization device for detecting placement of the tube 10 and/or physiological parameters of the patient. In such embodiments, the system 8 may also include a monitor 70 that may be configured to implement embodiments of the present disclosure and that may be coupled to the proximal end 26 via connector 72 (e.g., a USB connector) and cable 74. It should be understood that the monitor 70 may be a stand-alone device or may, in embodiments, be integrated into a single device with, for example, the ventilator 47. The monitor 70 may include processing circuitry, such as a microprocessor 75 coupled to an internal bus and a display 76. In an embodiment, the monitor 70 may be configured to communicate with the tube via connector 72, to obtain signals from any sensors or visualization devices associated with the assembly end 30. The information may then be stored in mass storage device 78, such as RAM, PROM, optical storage devices, flash memory devices, hardware storage devices, magnetic storage devices, or any suitable computer-readable storage medium. The information may be accessed and operated upon according to microprocessor 75 instructions. The monitor 70 may be configured to provide indications of tube placement within the trachea, such as an audio, visual or other indication, or may be configured to communicate the information to another device, such as the ventilator 47. In embodiments in which the assembly end 30 includes sensors or visualization devices, the monitor 70 may also provide drive signals (e.g., a drive signal to any associated light sources) to the sensor or camera structure on the assembly end 30.

Figure 2:
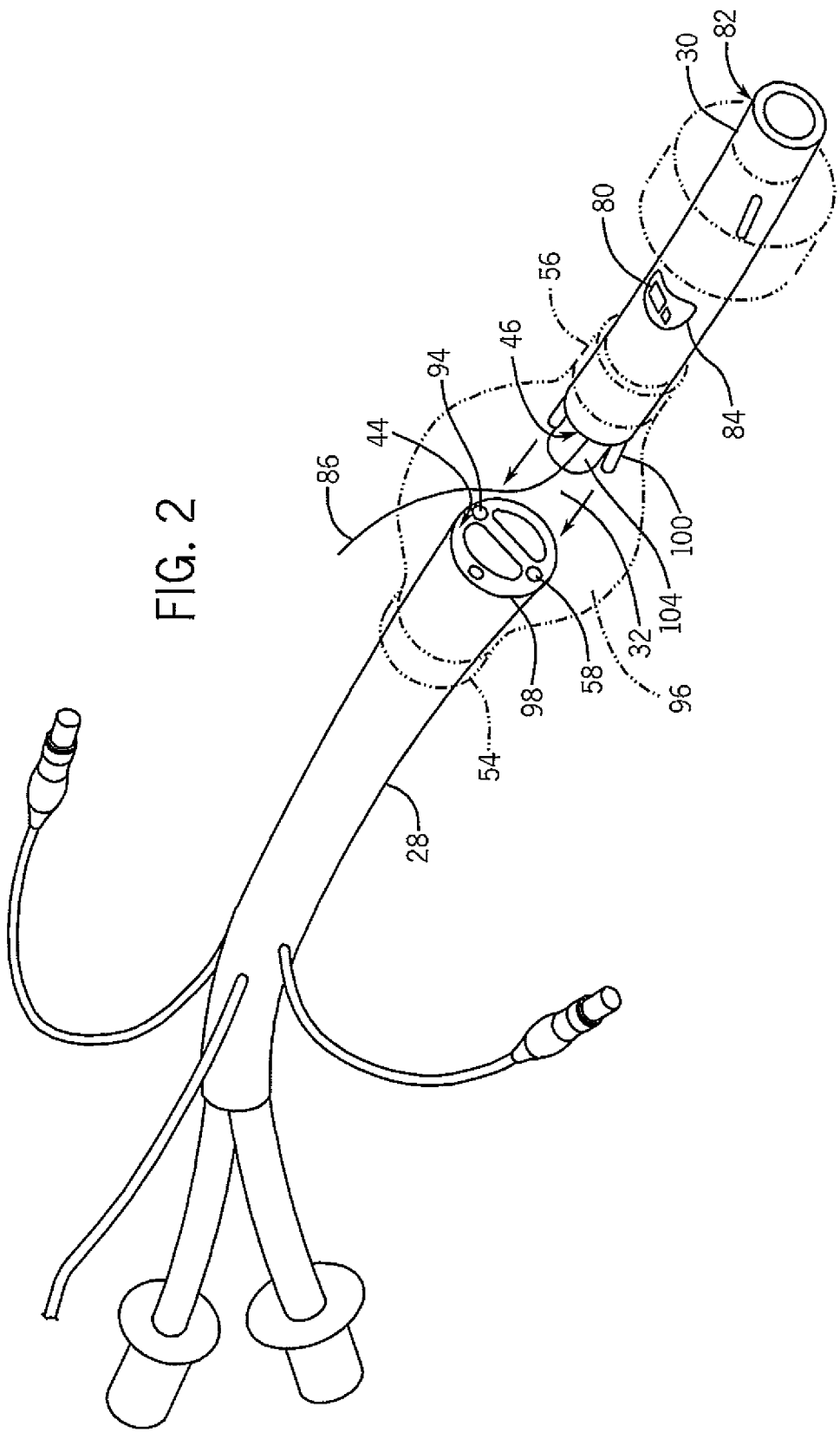
FIG. 2 is an exploded of an endobronchial tube including an assembly end in accordance with aspects of the present disclosure.

As noted, sensors or visualization devices may be associated with the assembly end 30 as appropriate. The tracheal tubes provided herein may include integral cameras that facilitate proper placement of the tube 10. In other embodiments, the assembly end 30 may include physiological parameter sensors, such as gas or tissue constituent sensors (e.g., carbon dioxide, oxygen) or other types of sensors to corroborate tube placement (e.g., optical sensors, magnetic sensors, ultrasound transceivers). FIG. 2 is an exploded view of the proximal portion 28 and the assembly end 30 of an exemplary endobronchial tube 10. In the illustrated embodiment, the assembly end 30 includes a camera or other image gathering component that is suitably sized and shaped to be incorporated into the assembly end 30, e.g., a CMOS chip camera. Other suitable image gathering components may include pixel arrays. During manufacturing, the camera 80 may be molded in place on the assembly end 30. That is, the component or components of the assembly end 30 may include a positioning feature that hold the camera 80 in place while the material that forms the exterior surface 82 is molded or hardened into shape. In this manner, the exterior surface 82 may form a recess 84 or housing around the camera 80 that may protect the optical features and/or orient the field of view.

The supporting circuitry and electronic components for the camera, such as connecting leads 86 from the camera 80, including any light pipes for light sources (e.g., light emitting diodes or fiber optic light sources), may be molded into (e.g., overmolded or embedded within) the exterior surface 82 to further affix the camera 80 to the tubular body 12. As noted, this embedding may take place during the forming of the assembly end 30, eliminating separate adhesion steps for the camera 80. During manufacturing, a portion of the leads 86 that extend from the proximal end of the assembly end may be threaded through a dedicated lumen 94 on the proximal portion. Once the leads 86 are threaded into the lumen 94, they may serve to further couple the assembly end 30 and the proximal portion 28.

The coupling between the proximal portion 28 and the assembly end 30 may be achieved by any suitable method, including one or more of adhesion, heat bonding, mechanical fastening, and compression fitting. Further, other structures on the tube 10 may contribute to the coupling strength. As shown, the coupling site 32 is positioned on the tubular body 12 in the space 96 enclosed by the tracheal cuff 52. In such an embodiment, the cuff 52, applied to the tube 10 after coupling the proximal portion 28 and the assembly end 30, acts as an additional coupling mechanism. Further, if the coupling seal is not airtight, any leaks vent to the interior of the cuff 52, which is also sealed relative to the outside space. Accordingly, the cuff 52 may act to further seal the coupling site 32 and provide additional securing force between the proximal portion 28 and the assembly end 30 to prevent the assembly end 30 from becoming dislodged. The cuff 52 is inflated via lumen 58, which communicates with the space 96 through notch 98. The coupling between the assembly end 30 and the proximal portion 28 may take advantage of the distal portion 98 of the lumen 58, which is unused. Barb 100, which protrudes from the proximal end 46 of the assembly end 30, may be sized and shaped to fit into the distal portion 98 of the lumen 58 to seal the end of the lumen during the coupling of the proximal portion 28 and the assembly end 30. To facilitate the coupling, the barb may be formed from a relatively rigid thermoplastic material that is more rigid than other portions of the assembly end 30. Additional barbs 100 may be positioned within other lumens. For example, a barb 100 may be positioned within lumen 64. However, because this lumen 64 is in fluid communication with the bronchial cuff 62, the barb 100 may be hollow to allow air to flow through. The assembly end 30 may also include additional formed features, such as protrusion 104, to provide adhesion surfaces. Further, these formed features may be used to correctly align the more proximal portion 34 of the tracheal ventilation lumen 14 and the more distal portion 36 of the tracheal ventilation lumen 14 as well as the more proximal portion 40 and more distal portion 42 of the bronchial ventilation lumen (see FIG. 1).

It should be noted that, while in presently contemplated embodiments the devices or components affixed on the assembly end will be permanently joined to the proximal portion, it is also possible to form the assembly end as a removable or serviceable structure. Thus, where desired, the assembly end may be removed and examined, reused, or at least partially disassembled or otherwise serviced, as needed.

Because endobronchial tubes are specifically designed for the anatomy of the right or left-mainstem bronchus, the built-in visualization devices may be positioned on the tube 10 to address specific challenges presented by the unique anatomic differences (e.g. right upper lobe occlusion). For example, the camera 80 may be positioned to visualize a lower portion of the tracheal space. During operation, the endobronchial tube 10 is inserted into the trachea of a patient and positioned within the left or right bronchial stem and the tracheal cuff 52 and bronchial cuff 62 are inflated to isolate the appropriate airway structures. The coupling site 32 is positioned generally in the tracheal space such that the proximal portion 28 is in the upper airway. The assembly end 30 includes the distal portion 42 of the bronchial ventilation lumen, including the transition in which the dividing wall 26 exits the dual-lumen portion of the tube 10 and extends distally to form part of the exterior surface 82 of the assembly end 30.

Figure 3:
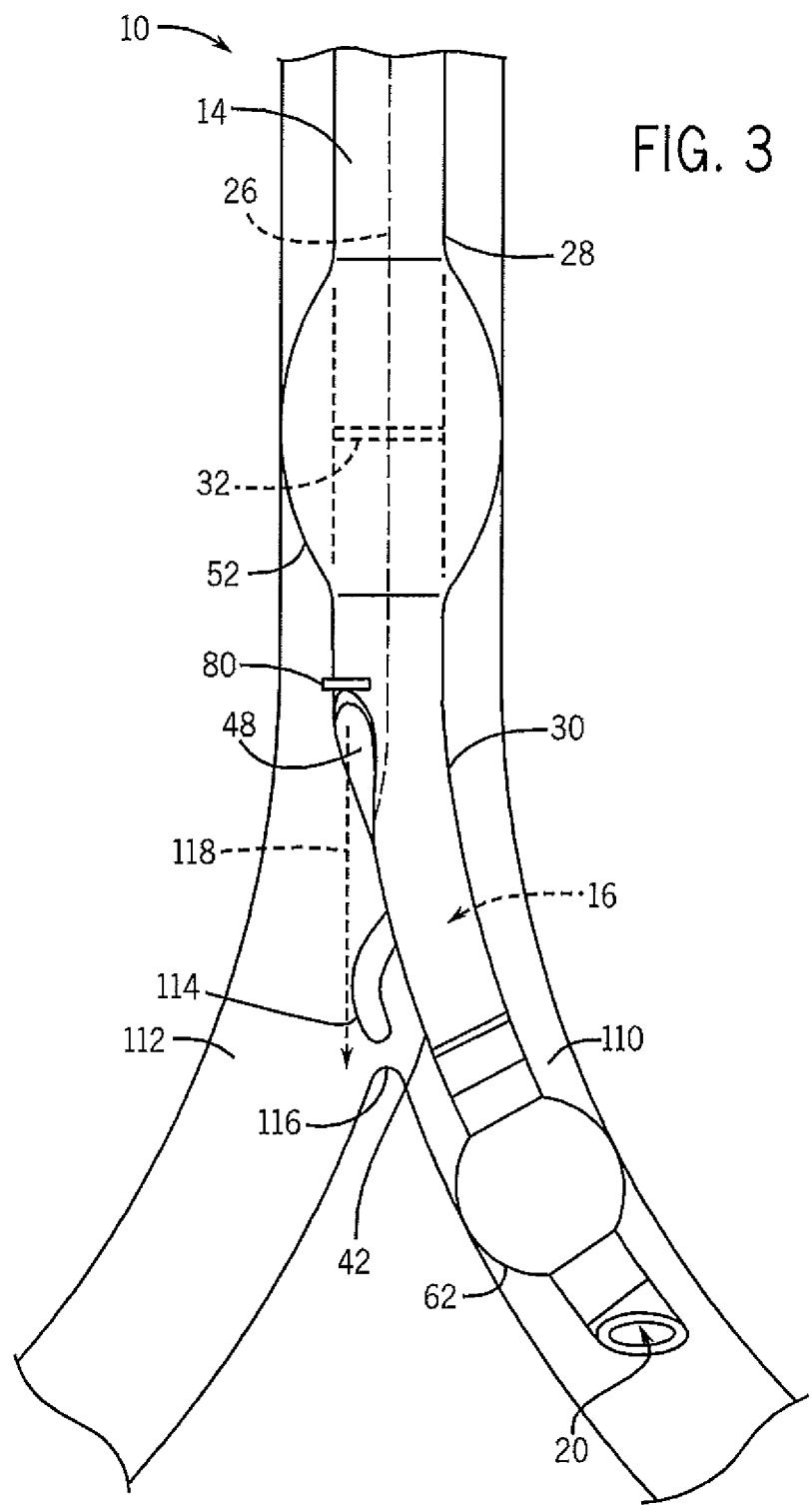
FIG. 3 is a perspective view of an exemplary endobronchial tube positioned within the left bronchus of a patient.

In certain embodiments, a tracheal tube 10 may be configured to be positioned within a left bronchial stem 110, as shown in FIG. 3. In such an embodiment, the tube 10 may have particular features that assist in positioning the distal portion 42 of the bronchial ventilation lumen 16 and the bronchial cuff 62. For example, relative to the right bronchial stem 112, the left bronchial stem is relatively curved. Accordingly, the distal portion 42 may be curved in a similar manner. Further, the tube 10 may include a hook 114 to help position the tube 10 relative to the patient's carina 116. After insertion of the tracheal tube 10, the camera 80 may be positioned so that its field of view is generally oriented in a distal direction (indicated by arrow 118). Such an orientation may allow viewing of the carina 116 or one or both of the left bronchus 110 or the right bronchus 112, which in turn may allow information about the placement of the tube 10 to be determined. In particular embodiments, it may be advantageous to align the camera 80 anterially. For example, the camera 80 may be positioned on the portion of the tubular body 12 that touches the anterior wall of the trachea when inserted. In particular, for a left-sided or right-sided bronchial tube, anterior alignment may be advantageous. In addition, it may be advantageous to affix the camera 80 on the bronchial ventilation lumen 16 below the tracheal lumen distal opening 48 but proximal to the carina 116. In alternative embodiments, different assembly ends 30 may correspond to either left-stem insertion or right-stem insertion.

Depending on the desired functionality of the tube 10, the assembly end 30 may include larger or smaller portions of the length of the tubular body 12. For example, FIG. 4 shows a tube 10 in which the coupling site 32 is located proximal to the proximal shoulder 54 of the tracheal cuff 52. Such an arrangement may be beneficial if the tube 10 includes one or more sensors located above the cuff 52. In certain embodiments, the cuff 52 may be applied to the tube 10 after the proximal portion 28 and the assembly end 30 are affixed to one another. In one embodiment, the proximal shoulder 54 may cover the coupling site 32 to seal and secure the coupling of the proximal portion 28 and the assembly end 30. The sensors may be molded into or formed integrally with that assembly end 30. It is also envisioned that the tube 10 as provided herein may be manufactured with standard proximal portions 28 and interchangeable assembly ends 30. During manufacturing, the appropriate assembly end 30 may be selected depending on the desired functionality (e.g., type and position of sensors or visualization devices), size (e.g., some assembly ends 30 may longer or shorter, or may have customized shapes or diameters), and/or materials (e.g., particular assembly ends may be formed from specialized materials). Accordingly, the assembly end 30 may provide increased manufacturing flexibility relative to tubes that are extruded in a single section.

Various embodiments described herein may allow for substantial economies of scale in the formation of relatively standard tubes (proximal portions) with specialized devices designed, dimensioned, and assembled as assembly ends. These may be pre-affixed to the tubes in a factory setting, or may be selected as needed and associated with a standard tube, providing a wide range of possible end products that may be selected depending upon corresponding patient needs.

As mentioned above, the assembly ends 30 or portions as provided herein may also be used in conjunction with single-lumen tubes. In one embodiment, the assembly end 30 may be used to customize the diameter of one portion of the tube. FIG. 5 illustrates a tube 10 that includes an assembly end 30 with a smaller diameter section 120. Such an implementation may be used to reduce the profile of a tracheal sealing cuff 52 against the tubular body 12. For patients with narrow airways, even a small protrusion of the cuff 52 relative to the tube 10 may present challenges during intubation. Accordingly, all or part of the portion of the tubular body 12 covered by the cuff 52 may be part of the smaller diameter section 120. While extruded tubes may have relatively thin walls to maximize the inner diameter, shown as diameter $d_1$ in the proximal portion 28, the extrusion process may be limited to compatible materials and that are extruded at a certain wall thickness to maintain the structural integrity of the tubular body 12. However, using a different manufacturing process for the assembly end 30 may allow different subset of materials to be used, which in turn may allow the wall thickness in section of the assembly end 30 to be reduced. Reducing the wall thickness results in a corresponding increase in the inner diameter $d_2$ in the smaller diameter section, which may result in a substantially constant and relatively larger internal diameter through the assembly end 30. While the depicted embodiment includes a coupling site 32 positioned above the cuff 52, the assembly portion may be coupled to the tubular body 12 at any suitable location.

The assembly end 30 may also include one or more subassemblies, as illustrated in exploded view in FIG. 6. The assembly end 30 may provide additional manufacturing flexibility by having interchangeable components with different functionality or features. In the depicted embodiment, the assembly end may include subassembly components 30a and 30b. At its proximal end 46, the subassembly 30a may include coupling features for the proximal portion 28 (see FIG. 1) such as barb 100 and surface 104 as well as additional features for coupling to subassembly 30b. Subassembly 30b may also include one or more coupling features (e.g. barb 100 or surface 104), which may be oriented to prevent misapplication directly to the proximal portion 28.

Figure 7:
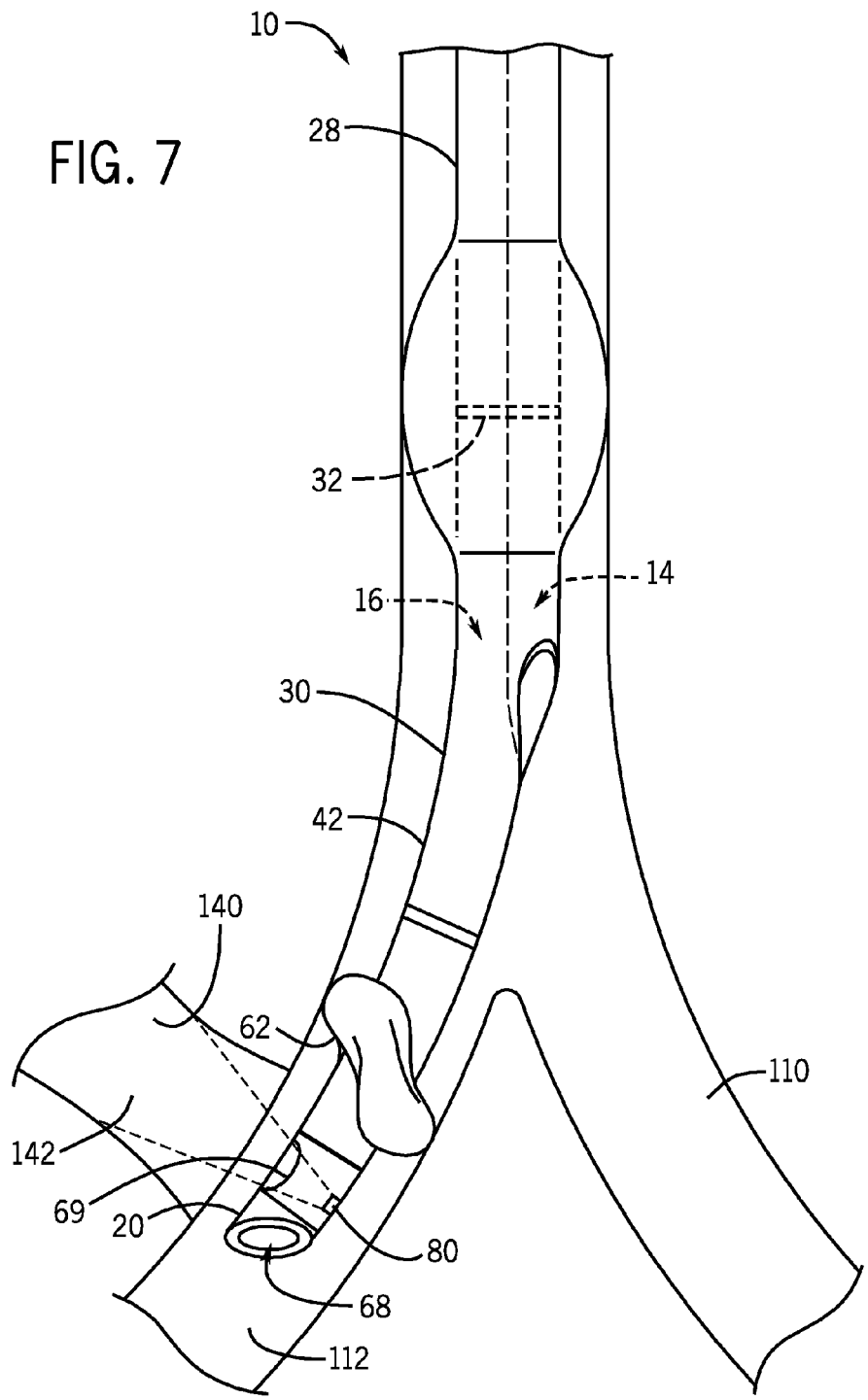
FIG. 7 is a perspective view of an exemplary endobronchial tube positioned within the right bronchus of a patient.

In a particular embodiment, the subassembly 30b may be used to position a camera 80 near the bronchial cuff 62. FIG. 7 illustrates a tracheal tube 10 that is configured to be positioned within a right bronchial stem 112. Because the right stem is relatively straighter than the left bronchial stem 110, the distal portion 42 of the tube 10 may have less of a curve. In addition, the bronchial cuff 62 may be shaped, for example with an S-shape, to provide an improved seal. Relative to a left-sided bronchial tube, a right-sided tube presents additional challenges related to the insertion of the tube 10. Proper insertion may involve aligning the distal end 20 of the bronchial ventilation lumen 16 with respect to an upper right bronchus 140. However, because this feature branches off to the side of the right bronchial stem 122, visualization through the distal opening 68 is difficult. Provided herein are tubes 10 that include a camera 80 positioned so that its field of view 142 extends through the side eye or fenestration 69 to permit visualization of the upper right bronchus 140. As depicted, an endobronchial tube may include a camera 80 positioned on the tubular body 12 vertically aligned and circumferentially opposite the side eye 69 (e.g., Murphy eye or fenestration) at the distal end 20 of the bronchial ventilation lumen 16. In particular embodiments, the camera assembly may be at least partially embedded in the tubular body so that inner diameter loss in the bronchial ventilation lumen 16 is minimized. It should be understood that in addition to the depicted camera 80, the assembly end 30 may also include additional camera 80, e.g., associated with the distal end 18 of the tracheal ventilation lumen 14.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheal tube, comprising:
    a proximal portion comprising a first portion of a ventilation lumen; and
    a distal portion separate from the proximal portion comprising a second portion of the ventilation lumen, wherein the second portion of the ventilation lumen comprises a first lumen and a second lumen, and wherein the first lumen is longer than the second lumen; and
    a coupling feature disposed on the proximal portion and configured to mate with a complementary feature on the distal portion such that the first and second portions of the ventilation lumens form a continuous passageway.

2. The tracheal tube of claim 1, wherein the proximal portion and the distal portion are formed from different materials.

3. The tracheal tube of claim 1, wherein the proximal portion is extruded and the distal portion is molded.

4. The tracheal tube of claim 1, comprising a cuff disposed around the proximal portion and the distal portion such that the cuff encircles the coupling between the proximal portion and the distal portion.

5. The tracheal tube of claim 4, comprising a second cuff disposed around the distal portion.

6. The tracheal tube of claim 1, wherein the distal portion comprises a camera.

7. The tracheal tube of claim 6, wherein the proximal portion comprises a passage adapted to accommodate an electrical coupling of the camera that extends from the distal portion.

8. The tracheal tube of claim 1, wherein the tracheal tube is configured to be coupled to at least one of a ventilator, a bag for ventilation, inspiration valving, expiration valving, or an air supply.

9. The tracheal tube of claim 1, wherein the tracheal tube comprises an endobronchial tube.

10. A tracheal tube, comprising:
    an extruded dual-lumen tube comprising a first lumen and a second lumen;
    a molded dual-lumen tube comprising a third lumen and a fourth lumen that is longer than the third lumen, wherein the molded dual-lumen tube is coupled to the extruded dual-lumen tube such that the first lumen and the third lumen are aligned to form a tracheal ventilation lumen and the second lumen and the fourth lumen are aligned to form a bronchial ventilation lumen; and
    a coupling feature disposed on a distal end of the extruded dual-lumen tube and configured to mate with a complementary feature on a proximal end of the molded dual-lumen tube to couple the molded dual-lumen with the extruded dual-lumen.

11. The tracheal tube of claim 10, wherein an inner diameter of the bronchial ventilation lumen is not constant along its length.

12. The tracheal tube of claim 11, wherein the inner diameter of at least a portion of the fourth lumen is larger than an inner diameter of the second lumen.

13. The tracheal tube of claim 1, wherein the coupling feature comprises one or more openings disposed on a distal end of the proximal portion, and wherein the complementary feature comprises one or more protrusions disposed on a proximal end of the distal portion.

14. The tracheal tube of claim 13, wherein the one or more protrusion are configured to seal at least one of the one or more openings.

15. The tracheal tube of claim 13, wherein the one or more protrusions form Pa of a cuff inflation lumen.

16. The tracheal tube of claim 1, comprising a first diameter section and a second diameter section, wherein the first diameter section has a larger diameter than the second diameter section, and wherein the second diameter section is surrounded by the cuff.

17. The tracheal tube of claim 10, comprising a first cuff disposed around the extruded dual-lumen tube and the molded dual-lumen tube such that the cuff encircles the coupling between the extruded and molded dual-lumen tubes.

18. The tracheal tube of claim 10, wherein the extruded dual-lumen tube and the molded dual-lumen tube are coupled proximal to a cuff surrounding the tracheal and bronchial ventilation lumens.

19. The tracheal tube of claim 10, comprising a second cuff disposed on the molded dual-lumen tube and surrounding the bronchial ventilation lumen.

* * * * *